US012788284B1

(12) United States Patent
Beckley et al.

(10) Patent No.: US 12,788,284 B1
(45) Date of Patent: Nov. 10, 2026

(54) WEARABLE DEVICE FOR CONTINUOUS MONITORING OF TARGET HORMONES AND/OR OTHER ANALYTES, AND METHODS OF USING THEREOF

(71) Applicant: MFB Fertility, Inc., Boulder, CO (US)

(72) Inventors: Amy Beckley, Erie, CO (US); Evyn White, Colorado Springs, CO (US)

(73) Assignee: MFB Fertility, Inc., Erie, CO (US)

( * ) Notice: Subject to any disclaimer, the term of this patent is extended or adjusted under 35 U.S.C. 154(b) by 853 days.

(21) Appl. No.: 18/106,834

(22) Filed: Feb. 7, 2023

Related U.S. Application Data

(60) Provisional application No. 63/307,544, filed on Feb. 7, 2022.

(51) Int. Cl.
*A61B 5/145* (2006.01)
*A61B 5/00* (2006.01)
*A61B 5/1473* (2006.01)

(52) U.S. Cl.
CPC ........ *A61B 5/14546* (2013.01); *A61B 5/1473* (2013.01); *A61B 5/6833* (2013.01); *A61B 5/685* (2013.01); *A61B 2560/0223* (2013.01)

(58) Field of Classification Search
None
See application file for complete search history.

(56) References Cited

U.S. PATENT DOCUMENTS

| | | | | |
|---|---|---|---|---|
| 11,029,321 B2 | 6/2021 | Beckley | | |
| 11,061,026 B2 | 7/2021 | Beckley | | |
| 11,131,665 B1 | 9/2021 | Beckley | | |
| 11,573,225 B2 | 2/2023 | Beckley | | |
| 12,061,196 B2 | 8/2024 | Koudele et al. | | |
| 12,181,465 B2 | 12/2024 | Beckley | | |
| 12,282,029 B2 | 4/2025 | Beckley | | |
| 2012/0088990 A1* | 4/2012 | Bunge | A61B 5/14735 | 600/300 |
| 2018/0321251 A1 | 11/2018 | Beckley | | |
| 2019/0223795 A1* | 7/2019 | Patolsky | A61B 5/14865 | |
| 2020/0078781 A1 | 3/2020 | Beckley | | |
| 2021/0055310 A1 | 2/2021 | Beckley | | |
| 2021/0389311 A1 | 12/2021 | Beckley | | |

(Continued)

FOREIGN PATENT DOCUMENTS

| | | |
|---|---|---|
| WO | WO-2019133920 A1 | 7/2019 |
| WO | WO-2021034412 A1 | 2/2021 |

(Continued)

OTHER PUBLICATIONS

Leiva et al., (2017). "Urinary luteinizing hormone Tests: Which concentration Threshold Best Predicts Ovulation?" Front. Public Health, 5:320, 8 pages.

(Continued)

*Primary Examiner* — Jay B Shah
(74) *Attorney, Agent, or Firm* — MORRISON & FOERSTER LLP

(57) ABSTRACT

Provided herein are wearable devices and methods for continuous monitoring of one or more target hormones and/or other analytes in a subject. For example, the device may be a wearable skin patch for continuous monitoring of luteinizing hormone, estrogen, progesterone, or human chorionic gonadotrophin, or a metabolite of any of the foregoing, as part of an ovulation test.

25 Claims, 5 Drawing Sheets

(56) References Cited

U.S. PATENT DOCUMENTS

| | | | |
|---|---|---|---|
| 2022/0146408 | A1 | 5/2022 | Koudele et al. |
| 2022/0341951 | A1 | 10/2022 | Beckley et al. |
| 2023/0064561 | A1 | 3/2023 | Beckley |
| 2023/0068803 | A1 | 3/2023 | Heikenfeld et al. |
| 2023/0408512 | A1 | 12/2023 | Beckley |
| 2024/0058805 | A1 | 2/2024 | Beckley |
| 2025/0035652 | A1 | 1/2025 | Beckley |
| 2025/0116677 | A1 | 4/2025 | Beckley |
| 2026/0070053 | A1 | 3/2026 | Beckley |

FOREIGN PATENT DOCUMENTS

| | | | |
|---|---|---|---|
| WO | WO-2022104326 | A1 | 5/2022 |
| WO | WO-2023069366 | A1 | 4/2023 |

OTHER PUBLICATIONS

U.S. Appl. No. 18/094,261, filed Jan. 6, 2023 titled "System for Evaluating Urine for the Presence or Absence of Pregnanediol Glucuronide and Other Hormones and Analytes."

U.S. Appl. No. 18/106,834, filed Feb. 7, 2023 titled "Wearable Device for Continuous Monitoring of Target Hormones and/or Other Analytes, and Methods of Using Thereof."

U.S. Appl. No. 18/125,590, filed Mar. 23, 2023 titled "Systems and Methods for Tracking Progesterone."

U.S. Appl. No. 29/788,306, filed Apr. 29, 2021 titled "Female Health Application User Interface."

U.S. Appl. No. 19/088,761, filed Mar. 24, 2025 titled "Portable Diagnostic System for Ovulation Cycle Monitoring."

* cited by examiner

WEARABLE DEVICE FOR CONTINUOUS MONITORING OF TARGET HORMONES AND/OR OTHER ANALYTES, AND METHODS OF USING THEREOF

CROSS-REFERENCE TO RELATED APPLICATIONS

This application claims priority to U.S. Provisional Patent Application No. 63/307,544, filed Feb. 7, 2022, which is incorporated herein by reference in its entirety.

FIELD

The present disclosure relates generally to wearable devices, and more specifically to a wearable device for continuous monitoring of one or more target hormones and/or other analytes in a subject. For example, the device may be a wearable skin patch for continuous monitoring of luteinizing hormone and progesterone, or a metabolite thereof, as part of an ovulation test.

BACKGROUND

A variety of devices attempt to detect hormone levels to allow for better understanding of the menstrual cycle. For example, it is well known in the art to utilize urine-based tests to detect luteinizing hormone (LH) in urine to assess the fertility status of a subject woman. In another example, blood testing has been utilized to evaluate for the presence of progesterone to confirm ovulation. In association with such tests, the timing of the testing remains critically important. If the subject woman neglects to time the test to correlate with a LH surge, for example, the subject woman may miss the signal that she is in a state of elevated fertility and may therefore miss a chance to conceive. As the various hormones associated with the menstrual cycle vary on different days and times within the menstrual cycle, it remains a challenge to estimate when testing should precisely take place.

A variety of other challenges remain in association with hormone testing. In the context of urine testing, in a situation where a subject woman is over-hydrated, her urine may become diluted. In such case, the woman's hormonal concentration in urine may fall below levels perceptible to a urine test. Furthermore, collecting a sample of blood or urine to evaluate hormone levels remains inconvenient and sometimes not accessible to women. It therefore remains desirable to have an alternative test that does not require a woman to estimate the proper time for or undergo the inconvenience of urine and blood testing. Ovulation-related hormones like LH can be very transient. A woman desiring to detect her LH surge could miss an ovulation signal if she doesn't collect her sample at the right time or doesn't sample it enough times per day. In other contexts such as drug testing, the user could over hydrate and cause a false negative result, causing a potentially dangerous situation.

BRIEF SUMMARY

In some aspects, provided is a device configured to continuously monitor bodily fluids for an increase in the presence of one or more target analytes, which includes one or more hormone(s) and/or other analyte(s). The device affixes to the skin of a subject woman. It collects interstitial fluid through the skin of the subject woman following application to the skin. Following detection of the targeted analyte(s), the device provides an indication that the analyte (s) is/are present.

In certain aspects, provided is a device configured to affix onto the skin of a subject and to continuously monitor bodily fluid of the subject for an increase in the presence of one or more target hormones and/or other analytes. In some embodiments, the device comprises one or more needles, a primary membrane, a secondary membrane, and a fluidic channel. The needles are configured to pierce the skin to collect the bodily fluid of the subject. In some variations, the primary membrane is on the side distal from the skin, and is coated with at least one analyte layer, optionally conjugated to a carrier protein. It should be understood that, in some embodiments, the analyte layer comprises a layer of low-affinity binding proteins. In some embodiments, the analyte (which in one variation, is a low-affinity binding protein) is conjugated to a carrier protein that may be serve to improve binding to the primary membrane. Each analyte layer is bound to magnetic beads conjugated to a primary antibody directed towards the one or more target hormones and/or other analytes. After the one or more needles pierce the skin, the bodily fluid flows to and passes through the primary membrane. In some variations, the secondary membrane is coated with a secondary antibody that binds the target analyte-magnetic bead complex (also referred to herein as analyte-magnetic beads). In some variations, the fluidic channel is positioned in between the primary membrane and the secondary membrane, and the fluidic channel is configured to contain a buffer. In some embodiments, when the concentration of the one or more target hormones and/or other analytes in the bodily fluid is high enough, the one or more target hormones and/or other analytes compete for binding on the surface of the magnetic beads to yield analyte-magnetic beads that are freed from the primary membrane. In some embodiments, the freed magnetic analyte-magnetic beads traverses the fluidic channel to the secondary membrane, and at least a portion of the analyte-magnetic beads bind to the secondary membrane, to produce a visibly perceptible color on the side of the device distal to the skin.

In other embodiments, the device comprises: or more needles configured to pierce the skin of the subject when the device is affixed onto the skin; a primary membrane coated with, on the side distal from the skin, low-affinity binding proteins connected to magnetically coupled primary antibodies, wherein the primary antibodies are directed towards the target analytes (e.g, one or more target hormones and/or other analytes), and wherein each magnetically coupled primary antibody comprises a primary antibody coupled with one or more magnetic elements, such as colored magnetic beads; a secondary membrane coated with, on the side facing the primary membrane, secondary antibodies, and wherein the secondary membrane exerts magnetic force in a detection zone; and a fluidic channel between the primary membrane and the secondary membrane. After the one or more needles pierce the skin, bodily fluid of the subject flows through the primary membrane into the fluidic channel. When the bodily fluid comprises target analytes, a target analyte competitively binds to a magnetically coupled primary antibody to form a complex that is released from the low-affinity binding protein on the primary membrane. The released complex (i) traverses the fluidic channel towards the secondary membrane as a result of the magnetic force exerted by or applied on the secondary membrane that attracts the one or more magnetic elements, such as colored magnetic beads, present in the complex, and (ii) binds to a secondary antibody on the secondary membrane. Then, when a plurality of complexes aggregates in the detection zone, a visibly perceptible color on the side of the device distal to the skin is produced.

In other embodiments, the device comprises one or more needles, and a primary membrane. The needles are configured to pierce the skin to collect the bodily fluid of the subject. In some variations, the primary membrane is on the side distal from the skin, and is coated with a monolayer of DNA aptamers bound to colorimetric dye. Complexing of one or more target hormones and/or other analytes to the DNA aptamer liberates the colorimetric dye, producing an optical readout. In some variations, the dye comprises a Cy7 dye, wherein when bound to at least a portion of the DNA aptamers is clear, and once liberated, produces a visual color.

In some of the foregoing aspects, the devices provided here are configured to operate as an ovulation test for the subject. In some embodiments, the device is a wearable skin patch, configured to produce a visibly perceptible color upon detection of luteinizing hormone, estrogen, and progesterone, or a metabolite thereof, in the bodily fluid.

In other aspects, provided is a method of continuously monitoring an analyte in a bodily fluid of a subject using any of the devices described herein. In some embodiments, the method comprises: affixing the device onto the skin of the subject; and detecting a color change responsive to the presence or increase of one or more target hormones and/or other analytes. In some variations, upon affixing the device onto the skin of the subject, bodily fluid is collected through one or more needles, and flows to and passes through the primary membrane.

In one embodiment, a color change is detected when: one or more target hormones and/or other analytes competitively binds to the magnetic beads to yield analyte-magnetic beads that are freed from the primary membrane; the freed magnetic analyte-magnetic beads traverse through the fluidic channel to the secondary membrane; and at least a portion of the analyte-magnetic beads bind to the secondary membrane, to produce a visibly perceptible color on the side of the device distal to the skin.

In another embodiment, a color change is detected when one or more target hormones and/or other analytes complex to the DNA aptamer to liberate the colorimetric dye and produce an optical readout.

DESCRIPTION OF THE FIGURES

The present application can be understood by reference to the following description taken in conjunction with the accompanying figures.

In FIG. 6A, immobilized CRK bound to anti-LH antibodies is displaced by LH. In FIG. 6B, gradual displacement of CRK by LH is detectable in a range near 25 mIU/mL, the physiologically relevant concentration of LH.

FIG. 7A describes the experimental setup in Example 2, with visually observable magnetic beads coupled to anti-LH antibodies and bound to immobilized CRK where well 7010 represents Sample 1: beads bound to CRK; well 7020 represents visual positive control: no magnet; well 7030 represents Sample 2: beads bound to CRK; well 7040 represents visual negative control: buffer only; and well 7050 represents magnet negative control: no CRK. In FIG. 7B, the photographs show that samples (solid line box) remain brown at the bottom as beads do not migrate to magnet, consistent with positive control. Magnet negative control (dashed line box) demonstrates that in the absence of CRK, beads do migrate to magnet, leaving the well colorless. In FIG. 7C, the photographs show that absence of beads in sample well magnets (solid line boxes) and presence of brown beads on negative control (dashed line box) confirms experimental results.

DETAILED DESCRIPTION

Figure 1:
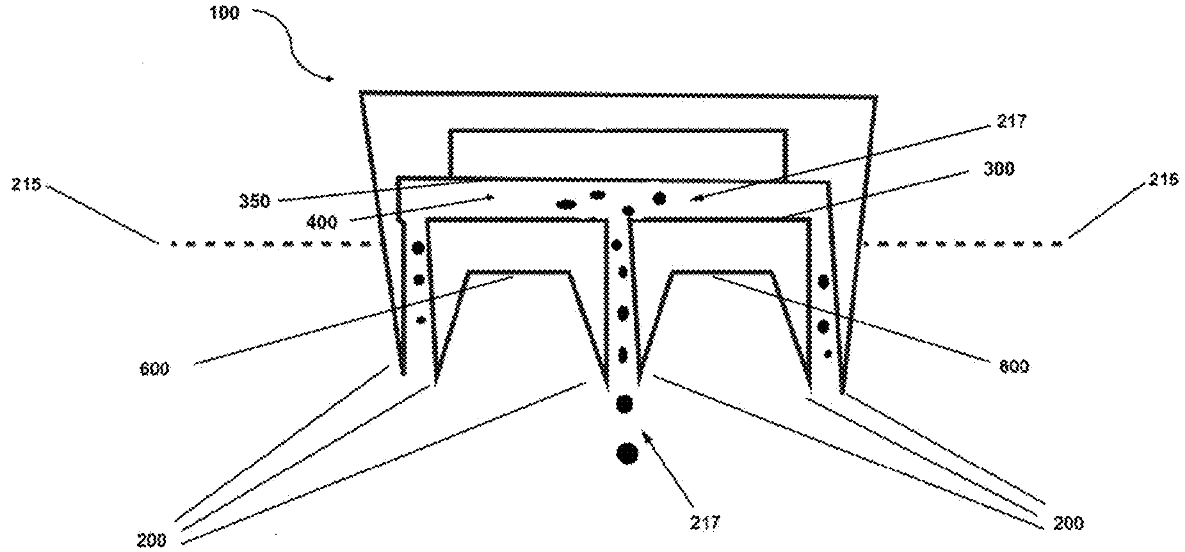
FIG. 1 depicts an exemplary device configured as a wearable skin patch.

The following description sets forth exemplary devices or systems, methods, parameters and the like. It should be recognized, however, that such description is not intended as a limitation on the scope of the present disclosure but is instead provided as a description of exemplary embodiments.

In some aspects, provided is a device configured to affix to the skin of a subject and continually monitor bodily fluid (such as interstitial fluid) collected through the subject's skin to detect the presence of at least one target analyte, or detect an increase of at least one target analyte. The target analyte may be one or more target hormones and/or other target analytes.

In some embodiments, at least one target analyte is luteinizing hormone (LH). A continuously monitoring solution for a hormone or other analyte, and in a particular example LH, provides advantages over other single point in time solutions (such as urine and blood tests). A wearable continuously monitoring test can be regularly checked with minimal inconvenience by the subject woman wearing the device over the course of a day. Thus, the devices and methods provided herein can improve the manner by which a subject detects when a LH surge occurs. In one variation, the device is particularly well-suited to detect LH because during ovulation LH is low, but a spike in LH (generally referred to as a "LH surge") causes the follicle to rupture and the release of an egg from the follicle, indicating high fertility. In one preferred configuration, the device provides more precise timing for the LH surge of its wearer.

In other embodiments, at least one target analyte is progesterone, or a metabolite thereof. In yet other embodiments, the device is configured to detect the presence of both LH and progesterone, or a metabolite thereof. In other embodiments, the device is configured to independently or additionally detect the presence of estrogen, or a metabolite thereof. In such embodiments, the device provided herein is particularly well-suited to evaluate for progesterone because after ovulation, a second hormone (following LH), progesterone, is produced which confirms that ovulation has occurred. Therefore, a configuration of the device to monitor both LH to detect the LH surge and progesterone to detect subsequent increase in progesterone after the surge could be useful for monitoring ovulation in a single menstrual cycle of a subject woman. In other embodiments, the device is configured to independently or additionally detect the presence of human chorionic gonadotropin (HCG), or a metabolite thereof. In such embodiments, the device provided herein is particularly well-suited for pregnancy detection. In such embodiments, the detection of HCG is indicative of a positive result for pregnancy. In some embodiments a positive result is obtained when the HCG concentration in the bodily fluid exceeds a certain threshold.

In yet other embodiments, the device is configured to detect the presence of one or more drugs. For example, in some variation, the device is configured to detect the presence of tetrahydrocannabinol (THC), opioids, or other recreational drugs in a subject.

Exemplary devices and components and configurations thereof, as well as methods of using such devices, are described in further detail below.

Wearable Skin Patch

In some aspects, provided is a device configured to affix onto skin of a subject and to continuously monitor bodily fluid of the subject for an increase in the presence of one or more target hormones and/or other analytes.

In some embodiments, the device is placed on the skin of a subject person. During placement of the device on the skin, one or more needles, such as microneedles, associated with the device pierce the skin to collect a bodily fluid (such as interstitial fluid).

For example, in one embodiment, one or more microneedles can either remain in the skin or be removed after puncture. The bodily fluid then flows to the primary membrane of the device. In some variations, the bodily fluid passes through the primary membrane, which on the side distal from the skin is coated with an analyte layer (optionally the same or very similar in structure to the targeted analyte for evaluation within the bodily fluid), optionally conjugated to a carrier protein. In certain embodiments, the analyte layer is bound to magnetic elements, such as magnetic beads, conjugated to a primary antibody directed towards the target analyte via low affinity binding. In one variation, the analyte layer comprises a layer of low-affinity binding proteins.

In some embodiments, the primary membrane is coated with, on the side distal from the skin, low-affinity binding proteins connected to magnetically coupled primary antibodies, wherein the primary antibodies are directed towards the target analytes. In some variations, each magnetically coupled primary antibody comprises a primary antibody coupled with one or more magnetic beads. In some variations of the foregoing embodiments, the magnetic beads are colored magnetic beads. In other variations, other suitable magnetic elements may be employed and coupled to the primary antibody.

In some variations, the low-affinity binding proteins are proteins that also bind the antibody but at a lower affinity than the target analyte. For example, in one embodiment of the device, the primary antibody is the LH antibody, which binds LH as its target analyte; and the low-affinity binding protein is the CRK protein, which is an adapter molecule crk (also known as proto-oncogene c-Crk) that in humans is encoded by the CRK gene. In certain embodiments, the low-affinity binding protein may be used alone or in conjugation to a carrier protein, in which the carrier protein may help to improve binding to the primary membrane. In some variations, the CRK protein may be directed connected to the primary membrane (e.g. via a coating). In other variations, the CRK protein may be conjugated with a carrier protein bound to the primary membrane. Suitable carrier proteins may include, for example, BSA, OVA, KLH, and BGG.

When the concentration of the target analyte in the bodily fluid is high enough, the target analyte will compete for binding on the surface of the magnetic microsphere (also referred to as the magnetically coupled primary antibody) to form a complex that is freed (or released) from the primary membrane. Upon binding to the target analyte, the antibody magnetic microsphere (or the complex that comprises the target analyte bound to the magnetically coupled primary antibody) travels through the fluidic channel space to the secondary membrane.

The directional travel of the magnetic beads (e.g., within the antibody magnetic microsphere or the complex described above) towards the secondary membrane is mediated by a magnetic force exerted by or applied on the secondary membrane that attracts the magnetic beads. In some variations, the secondary membrane exerts magnetic force in a detection zone. In other variations, a magnetic force is applied on the secondary membrane in a detection zone. In some embodiments, one or more small magnets or a magnetic coating is placed distal to the secondary membrane. In some variations, one or more magnets may be affixed to the secondary membrane, or one or more magnets may be positioned within the device in close proximity to the secondary membrane such that there is a sufficient magnetic force exerted to attract the complex (e.g., comprising the target analyte bound to the magnetically coupled primary antibody). In other embodiments, a magnetic membrane is employed. Any suitable techniques to achieve a magnetic force exerted by or applied by the secondary membrane may be employed in the device. The detection zone is an area of the device where the detection of the target analyte (e.g., one or more hormones and/or other analytes) may be visualized.

The secondary membrane is coated with a secondary antibody that binds that targeted analyte-magnetic bead complex (referring to the complex that comprises the target analyte bound to the magnetically coupled primary antibody). In some embodiments, this secondary antibody may bind a second epitope on the target analyte or the fragment crystallizable region (FC region) of the first antibody. In some variations, the Fc region of the primary antibody is what binds to the secondary antibody. In one variation of the device, if the primary LH antibody was produced in a mouse, then the secondary antibody is an anti-mouse antibody. Antibodies may be made in mice, rabbits, and goats, and the suitable secondary antibodies are anti-mouse, rabbit, and goat, respectively.

Once the complex that comprises that target analyte bound to the magnetically coupled primary antibody binds to the secondary membrane (e.g., via the secondary antibody), a visibly perceptible color (such as a dark color) will appear on the side of the device distal to the skin, e.g., in the detection zone of the device. This color results from the color of the magnetic bead (if an iron magnetic bead is utilized, the color generally is black; if a gold magnetic bead is utilized, the color generally is red) which becomes visible through the secondary membrane. The secondary membrane is visible to the user and will progressively turn darker as more targeted analyte-bound magnetic beads bind to the membrane. In other words, when a plurality of complexes aggregates in the detection zone, a visibly perceptible color on the side of the device distal to the skin is produced. The color depicted upon or within the device can be then read by eye or scanned using a smartphone camera. In an example, a curve depicting the color that appears correlating to a specific amount of targeted analyte-bound magnetic beads can be utilized to provide a quantitative estimate of the targeted analyte detected.

With reference to FIG. 1, depicted is an exemplary device configured as a wearable skin patch 100. Wearable skin patch 100 is configured as a sandwich assay. Wearable skin patch 100 comprises microneedles 200, which are oriented in a configuration to pierce skin 215 of the subject person wearing wearable skin patch 100. Microneedles 200 are configured to sample the blood, serum, and/or interstitial fluid 217 of the subject person. Wearable skin patch 100 further includes primary membrane 300 and secondary membrane 350. Blood, serum, and/or interstitial fluid 217 from the subject travels to primary membrane 300 and secondary membrane 350 through fluidic channel 400.

Figure 3:
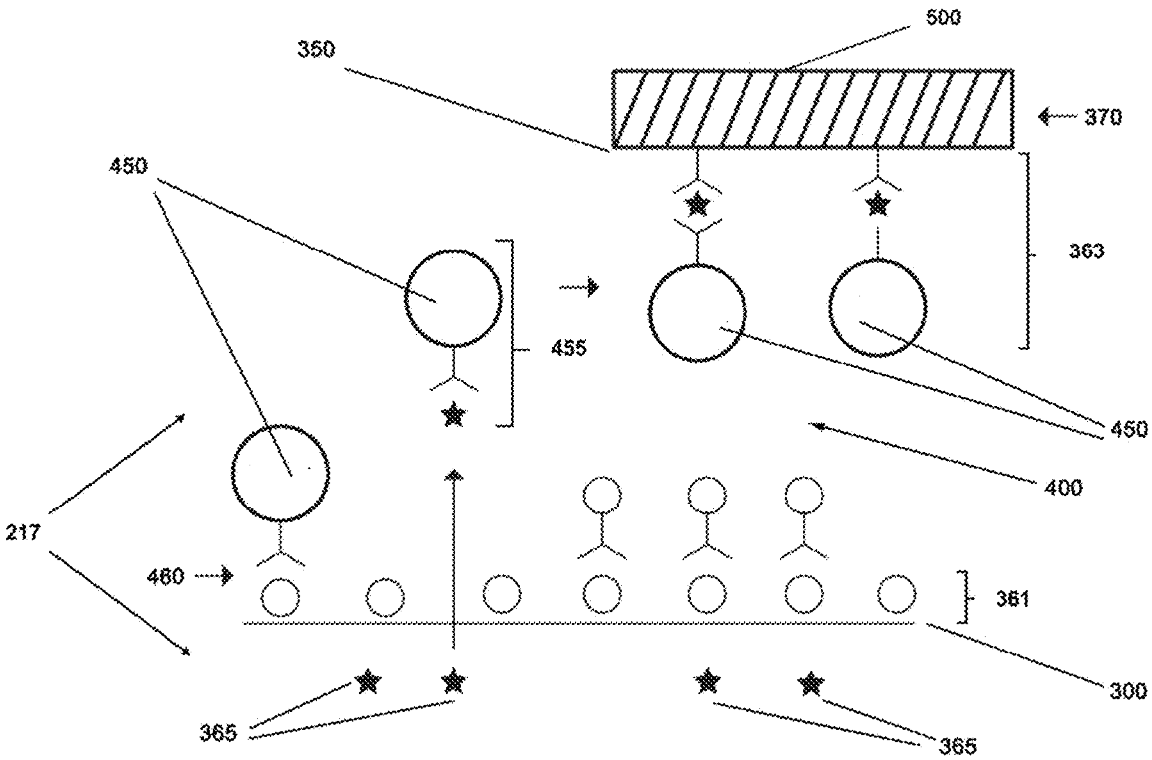
FIGS. 3 and 4 depict configurations of exemplary devices, showing the primary and secondary membranes and the fluidic channel of the devices.

With reference to FIG. 3, primary membrane 300 is coated on the side distal to the side intended for contact with skin 215 of the subject with coating 361 that includes one or more target analytes (which may be hormones and/or other analytes) bound to a carrier protein. In some embodiments, primary membrane 300 comprises a pore size to prevent proteins and/or analytes over 40 KD through. In one embodiment, primary membrane 300 comprises a pore size of about 30 KD. It should be understood that target analytes 365 may include one or more hormones and/or other analytes. For example, in some variations, target analytes 365 are luteinizing hormone (LH), estrogen, or a metabolite thereof, and/or progesterone, or a metabolite thereof. In some variations, the carrier protein comprises bovine serum albumin (BSA). When target analytes 365 contained in blood, serum and/or interstitial fluid 217 flow to and through primary membrane 300, target analytes 365 bind to antibody-coated magnetic beads 450 to form analyte-magnetic bead complex 455. Secondary membrane 350 is coated with a second antibody that binds to the analyte-magnetic bead complex, forming analyte coating 363. In some variations, the second antibody of secondary membrane 350 binds a second epitope on target analytes 365 or the fragment crystallizable region (FC region) of the first antibody.

Antibodies are conjugated to magnetic beads 450 and bound to primary membrane 300 via low affinity binding 460. The bodily fluid (referring in this example to interstitial fluid 217) containing target analytes 365 passes through the surface of primary membrane 300. When the concentration of target analytes 365 in the bodily fluid is high enough, target analytes 365 will compete for binding on the surface of magnetic beads 450 and free antibody-coated magnetic beads 450 from primary membrane 300. Upon binding to target analytes 365, antibody-coated magnetic beads 450 traverses fluidic channel 400 to secondary membrane 350. Secondary membrane 350 is visible to the subject (user) and will progressively turn darker as more analyte-magnetic bead complex 455 bind to the secondary membrane 350. Once analyte-magnetic bead complex 455 binds to secondary membrane 350, visibly perceptible color 370 is produced. In various embodiments, visually perceptible color 370 can be read by eye or scanned using a smartphone camera.

If visually perceptible color 370 is perceived via a smartphone camera, the threshold of a positive result can be quantitated or determined by the number of dark pixels. In some embodiments, the method comprises: sweeping the photographed wearable skin patch, or a cropped area of the photographed wearable skin patch; creating a vector of color values including the color values obtained from a plurality of horizontal pixel positions on the photographed wearable skin patch or cropped area of the photographed wearable skin patch; identifying the location of the perceptible color depicted within the wearable skin patch; and calibrating to determine a hormone or analyte level corresponding to a color value. In a typical case, the intensity of the pigmentation relative to hormone or analyte concentration can generally be curve fitted to a graph of a mathematical function. In such manner, each color value can be approximated to a hormone or analyte concentration. An example of such process is further described in U.S. patent application Ser. No. 17/522,696 filed on Nov. 9, 2021, hereby incorporated by reference with priority claimed thereto.

With reference again to FIG. 3, fluidic channel 400 comprises buffer. In some variations, the buffer comprises phosphate-buffered saline (PBS), saline, or hydrogel, or any combination thereof. It should be understood, however, in other exemplary embodiments, no buffer may be present in the fluidic channel. In such instances, the fluidic channel may be filled with the bodily fluid. In some embodiments, fluidic channel 400 allows for magnetic beads 450 to travel through the space of fluidic channel 400. In one embodiment, fluidic channel 400 has a width in the range of 10-900 microns.

In some embodiments, wearable skin patch 100 further comprises magnet or magnetic coating 500. The directional travel of magnetic beads 450 towards secondary membrane 350 is mediated by magnet or magnetic coating 500 located distally from secondary membrane 350 and primary membrane 300.

In some embodiments, wearable skin patch 100 further comprises adhesive 600. Adhesive 600 may coat all or a portion of the surface of wearable skin patch 100 proximal to skin 215 of the subject person wearing patch 100. In various embodiments, adhesive 600 is configured to affix wearable skin patch 100 to the subject person.

Figure 4:
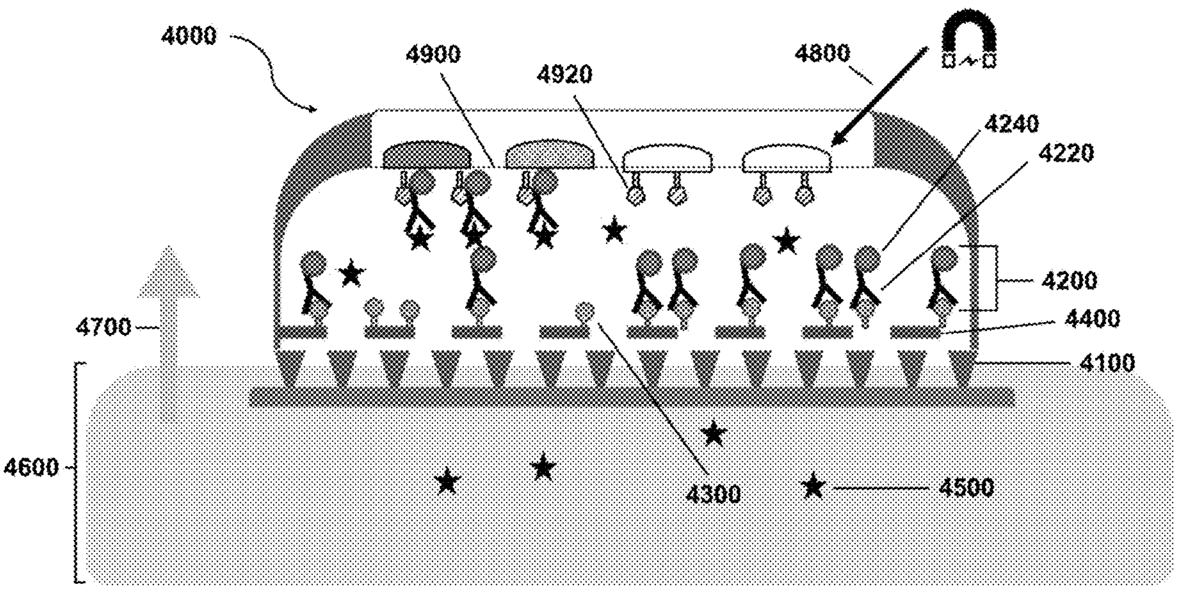

With reference to FIG. 4, another exemplary wearable skin patch 4000 for detecting LH is depicted. Hollow microneedles 4100 are coupled to an antibody-based flow through LH sensor. Magnetic bead-coupled anti-LH antibodies 4200, comprising primary antibody 4220 coupled with one or more magnetic beads 4240, are held via a low affinity binding protein 4300 on primary membrane 4400 of the sensor. Upon binding LH 4500 (the target analyte in this example) that is present in the bodily fluid (e.g., interstitial fluid) of the subject, the anti-LH antibody (the primary antibody in this example) is drawn to the upper detection zone where a color change will occur and determine the LH surge and onset of ovulation. Specifically, the antibody-based sensor in FIG. 4 includes two antibody binding surfaces. After one or more microneedles 4100 pierce the skin/dermis 4600, the bodily fluid will continually flow, in direction of bodily fluid flow 4700, through microneedles 4100. The bodily fluid will come into contact with primary membrane 4400 which is coated with low-affinity binding protein 4300 bound to magnetically coupled primary antibodies 4200. In this example, the primary antibodies are anti-LH antibodies. The use of low-affinity binding protein 4300 immobilizes the primary antibody (here, LH antibody) away from the detection zone. When the bodily fluid contains LH (the target analyte), the LH 4500 will bind the anti-LH antibody coupled to a magnetic bead (referring to magnetically coupled primary antibody 4200) and form a complex that travels towards the detection zone when a magnetic force 4800 is applied, and binds to one or more secondary antibodies 4920 on secondary membrane 4900. Therefore, as LH concentrations in the bodily fluid increase, the LH antibody will collect at the detection zone, producing a color. In some embodiments, the color is a black color. In some embodiments the color is a brown color. The color will be directly proportional to the amount of bound LH in the bodily fluid. In some embodiments, a phone application may be used to scan the patch and color saturation may be used to determine the amount of LH produced per hour and thus determine when the start of the LH surge has occurred and ovulation is imminent.

It should be understood that, in other exemplary embodiments, the wearable skin patch depicted in FIG. 4 may be configured to detect other target analytes. For example, in another embodiment, the patch may be configured to independently or additionally detect progesterone or a metabolites such as pregnanediol (PDG). In such embodiments, the primary antibody is an anti-progesterone or progesterone metabolite antibody. In yet another embodiment, the variation may be configured to independently or additionally detect human chorionic gonadotropic (HCG). In such embodiments, the primary antibody is an anti-HCG antibody. In such embodiments, the wearable skin patch is configured for pregnancy detection, where the detection of HCG is indicative of a positive result for pregnancy.

In other embodiments, the devices provided herein (such as the wearable skin patches) are configured to detect multiple hormones or analytes at the same time. In such embodiments, the primary membrane is coated with two or more antibody-bound magnetic beads and the secondary membrane comprises multiple different areas, each corresponding to a particular secondary reagent coated onto a particular area. In such configurations, the two or more different areas within the wearable skin patch produces color upon the detection of a particular hormone or analyte corresponding to the particular secondary reagent coated onto each particular area.

For example, in the case of an ovulation test, a wearable skin patch configured with multiple different areas could simultaneously detect for the presence of LH, estrogen and progesterone or a metabolite thereof in an applied bodily fluid. In an example of use of such configuration, the user could place the device on her skin, preferably on her torso near the belly button. She would wear the device started after the end of her menstrual cycle. Once she had a surge in LH, the color in the LH area would turn from white to dark. Then when her progesterone increased, the color in the progesterone (PDG) area would turn from white to dark as well. So a woman that has not ovulated would see an all white device. A woman that is about to ovulate and produced LH would be 1 line/area of dark color. Then, in one example, once she ovulated, she would see two lines/areas of color to account for the presence of LH and progesterone. At that point, the woman has successfully ovulated and can remove the device. The device could be replaced once daily or ideal, up to 14 days. Typically a woman would start using this device to track ovulation on the 5-10$^{th}$ day or her cycle and stop using it on the 14$^{th}$-23$^{rd}$ day of her cycle if her cycle length is the average length of 25-35 days.

Figure 2:
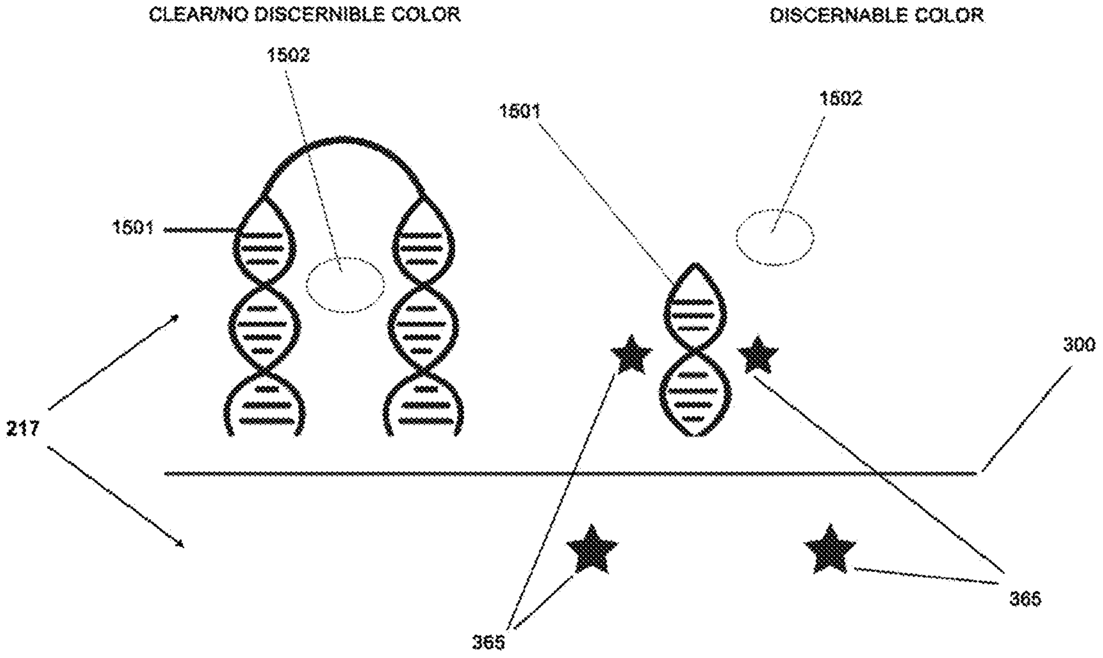
FIG. 2 depicts an exemplary aptamer configuration.

In other embodiments, the target hormones and/or other analytes can be detected via an aptamer-based displacement platform. With reference to FIG. 2, in some variations, the bodily fluid (referring in this example to interstitial fluid 217) is pulled from the body and contacts primary membrane 300 coated with a monolayer of DNA aptamers 1501 bound to a colorimetric dye 1502. The binding of target analytes 365 liberates dye 1502 that is complexed with aptamer 1501, producing an optical readout. In some variations, dye 1502 comprises a Cy7 dye that when bound to aptamer 1501 is clear, and once liberated, produces a visual color (optionally blue). In some embodiments, the sample is monitored for a color change. If a color change does not occur, then target analytes 365 are not present in interstitial fluid 217. If a color change does occur, the target analytes 365 are present in the interstitial fluid 217. The color change signifies that the target analytes 365 caused DNA aptamer 1501 to liberate colorimetric dye 1502. In some embodiments, the liberation of colorimetric dye 1502 is due to DNA aptamer 1501 undergoing a conformational change. The degree the color changes in response to the analyte 105 may be quantified by colorimetric quantification methods known to those of ordinary skill in the art.

The aforementioned aptamer-based approach and the antibody flow through approach for the devices described herein may both continually sense the target analytes (e.g., one or more hormones and/or other analytes) in the interstitial fluid via microneedles.

Enumerated Embodiments

The following enumerated embodiments are representative of some aspects of the invention.

1. A device configured to affix onto skin of a subject and to monitor bodily fluid of the subject for an increase in the presence of one or more target hormones and/or other analytes, comprising:
   - one or more needles configured to pierce the skin to collect the bodily fluid of the subject;
   - a primary membrane, wherein on the side distal from the skin, is coated with at least one analyte layer,
     - wherein each analyte layer is bound to magnetic beads conjugated to a primary antibody directed towards the one or more target hormones and/or other analytes,
     - wherein, after the one or more needles pierce the skin, the bodily fluid flows to and passes through the primary membrane,
   - a secondary membrane, coated with a secondary antibody that binds the target analyte-magnetic bead complex, and
   - a fluidic channel, positioned in between the primary membrane and the secondary membrane, wherein the fluidic channel is configured to contain a buffer;
   - wherein, when the concentration of the one or more target hormones and/or other analytes in the bodily fluid is high enough, the one or more target hormones and/or other analytes compete for binding on the surface of the magnetic beads to yield at least one analyte-magnetic bead complex that is freed from the primary membrane,
   - wherein the freed magnetic analyte-magnetic bead complex traverses the fluidic channel to the secondary membrane, and
   - wherein at least a portion of the analyte-magnetic bead complex binds to the secondary membrane, to produce a visibly perceptible color on the side of the device distal to the skin.
2. The device of embodiment 1, further comprising adhesive.
3. The device of embodiment 2, wherein the adhesive coats at least a portion of the surface of the device proximal to the skin of the subject wearing the device.
4. The device of any one of embodiments 1 to 3, wherein the primary membrane comprises a pore size to prevent proteins and/or analytes over 40 KD through.
5. The device of any one of embodiments 1 to 3, wherein the primary membrane comprises a pore size of about 30 KD.
6. The device of any one of embodiments 1 to 5, wherein one or more target hormones and/or other analytes is luteinizing hormone, estrogen or a metabolite thereof, or progesterone or a metabolite thereof.

7. The device of any one of embodiments 1 to 6, wherein the analyte layer is conjugated to a carrier protein.

8. The device of embodiment 7, wherein the carrier protein is bovine serum albumin.

9. The device of any one of embodiments 1 to 8, wherein one or more of the needles are microneedles.

10. The device of embodiment 9, wherein one or more needles, after piercing the skin, remain in the skin.

11. The device of embodiment 10, wherein one or more needles, after piercing the skin, are removed.

12. The device of any one of embodiments 1 to 11, wherein each analyte layer is bound to magnetic beads conjugated to a primary antibody directed towards the one or more target hormones and/or other analytes via low affinity binding.

13. The device of any one of embodiments 1 to 12, wherein the buffer comprises phosphate-buffered saline, saline, or hydrogel, or any combination thereof.

14. The device of any one of embodiments 1 to 13, wherein the fluidic channel has a width between 10 microns and 900 microns.

15. A device configured to affix onto skin of a subject and to monitor bodily fluid of the subject for an increase in the presence of one or more target hormones and/or other analytes, comprising:
- one or more needles configured to pierce the skin to collect the bodily fluid of the subject;
- a primary membrane, wherein on the side distal from the skin, is coated with a monolayer of DNA aptamers bound to colorimetric dye,
  - wherein complexing of one or more target hormones and/or other analytes to the DNA aptamer liberates the colorimetric dye, producing an optical readout.

16. The device of embodiment 15, wherein the dye comprises a Cy7 dye, wherein when bound to at least a portion of the DNA aptamers is clear, and once liberated, produces a visual color.

17. The device of any one of embodiments 1 to 16, wherein the device is configured to operate as an ovulation test for the subject.

18. The device of any one of embodiments 1 to 17, wherein the device is a wearable skin patch, configured to produce a visibly perceptible color upon detection of luteinizing hormone, estrogen or progesterone, or a metabolite thereof, in the bodily fluid.

19. The device of embodiment 18, wherein the device is configured to affix to the subject's torso near the belly button.

20. A method of continuously monitoring an analyte in a bodily fluid of a subject, comprising:
- affixing the device of any one of embodiments 1-19 onto the skin of the subject; and
- detecting a color change responsive to the presence or increase of one or more target hormones and/or other analytes.

21. The method of embodiment 20, wherein upon affixing the device onto the skin of the subject, bodily fluid is collected through one or more needles, and flows to and passes through the primary membrane, and
- wherein a color change is detected when:
  - one or more target hormones and/or other analytes competitively binds to the magnetic beads to yield at least one analyte-magnetic bead complex that is freed from the primary membrane,
  - the freed magnetic analyte-magnetic bead complex traverses through the fluidic channel to the secondary membrane, and
  - at least a portion of the analyte-magnetic bead complex binds to the secondary membrane, to produce a visibly perceptible color on the side of the device distal to the skin.

22. The method of embodiment 20, wherein upon affixing the device onto the skin of the subject, bodily fluid is collected through one or more needles, and flows to and passes through the primary membrane, and wherein a color change is detected when:
- one or more target hormones and/or other analytes complex to the DNA aptamer to liberate the colorimetric dye and produce an optical readout.

23. The method of any one of embodiments 20 to 22, wherein the method further comprises:
- photographing the device;
- sweeping the photograph of the device, or a cropped area of the device;
- creating a vector of color values including the color values obtained from a plurality of horizontal pixel positions on the photograph of the device or cropped area of the photograph of the device;
- identifying the location of the perceptible color depicted within the photograph of the device; and
- calibrating to determine a hormone or analyte level corresponding to a color value.

24. A device configured to affix onto skin of a subject and to monitor bodily fluid of the subject for an increase in the presence of one or more target hormones and/or analytes, comprising:
- one or more needles configured to pierce the skin to collect the bodily fluid of the subject;
- a primary membrane, wherein on the side distal from the skin, is coated with at least one analyte layer,
  - wherein each analyte layer is bound to magnetic beads conjugated to a primary antibody directed towards the one or more target hormones and/or analytes,
  - wherein, after the one or more needles pierce the skin, the bodily fluid flows to and passes through the primary membrane,
- a secondary membrane, coated with a secondary antibody that binds the target analyte-magnetic bead complex, and
- a fluidic channel, positioned in between the primary membrane and the secondary membrane, wherein the fluidic channel is configured to contain a buffer;
- wherein, when the concentration of the one or more target hormones and/or analytes in the bodily fluid is high enough, the one or more target hormones and/or analytes compete for binding on the surface of the magnetic beads to yield at least one analyte-magnetic bead complex that is freed from the primary membrane,
- wherein the freed magnetic analyte-magnetic bead complex traverses the fluidic channel to the secondary membrane, and
- wherein at least a portion of the analyte-magnetic bead complex binds to the secondary membrane, to produce a visibly perceptible color on the side of the device distal to the skin.

25. The device of embodiment 24, further comprising adhesive.

26. The device of embodiment 25, wherein the adhesive coats at least a portion of the surface of the device proximal to the skin of the subject wearing the device.
27. The device of any one of embodiments 24 to 26, wherein the primary membrane comprises a pore size to prevent proteins and/or analytes over 40 KD through.
28. The device of any one of embodiments 24 to 26, wherein the primary membrane comprises a pore size of about 30 KD.
29. The device of any one of embodiments 24 to 28, wherein one or more target hormones and/or analytes is luteinizing hormone, estrogen or a metabolite thereof, or progesterone or a metabolite thereof.
30. The device of any one of embodiments 24 to 29, wherein the analyte layer is conjugated to a carrier protein.
31. The device of embodiment 30, wherein the carrier protein is bovine serum albumin.
32. The device of any one of embodiments 24 to 31, wherein one or more of the needles are microneedles.
33. The device of embodiment 32, wherein one or more needles, after piercing the skin, remain in the skin.
34. The device of embodiment 33, wherein one or more needles, after piercing the skin, are removed.
35. The device of any one of embodiments 24 to 34, wherein each analyte layer is bound to magnetic beads conjugated to a primary antibody directed towards the one or more target hormones and/or analytes via low affinity binding.
36. The device of any one of embodiments 24 to 35, wherein the buffer comprises phosphate-buffered saline, saline, or hydrogel, or any combination thereof.
37. The device of any one of embodiments 24 to 36, wherein the fluidic channel has a width between 10 microns and 900 microns.
38. A device configured to affix onto skin of a subject and to monitor bodily fluid of the subject for an increase in the presence of one or more target hormones and/or analytes, comprising:
    one or more needles configured to pierce the skin to collect the bodily fluid of the subject;
    a primary membrane, wherein on the side distal from the skin, is coated with a monolayer of DNA aptamers bound to colorimetric dye,
    wherein complexing of one or more target hormones and/or analytes to the DNA aptamer liberates the colorimetric dye, producing an optical readout.
39. The device of embodiment 38, wherein the dye comprises a Cy7 dye, wherein when bound to at least a portion of the DNA aptamers is clear, and once liberated, produces a visual color.
40. The device of any one of embodiments 24 to 39, wherein the device is configured to operate as an ovulation test for the subject.
41. The device of any one of embodiments 24 to 40, wherein the device is a wearable skin patch, configured to produce a visibly perceptible color upon detection of luteinizing hormone, estrogen or progesterone, or a metabolite thereof, in the bodily fluid.
42. The device of embodiment 41, wherein the device is configured to affix to the subject's torso near the belly button.
43. A method of continuously monitoring an analyte in a bodily fluid of a subject, comprising:
    affixing the device of any one of embodiments 24-42 onto the skin of the subject; and
    detecting a color change responsive to the presence or increase of one or more target hormones and/or analytes.
44. The method of embodiment 43, wherein upon affixing the device onto the skin of the subject, bodily fluid is collected through one or more needles, and flows to and passes through the primary membrane, and
    wherein a color change is detected when:
    one or more target hormones and/or analytes competitively binds to the magnetic beads to yield at least one analyte-magnetic bead complex that is freed from the primary membrane,
    the freed magnetic analyte-magnetic bead complex traverses through the fluidic channel to the secondary membrane, and
    at least a portion of the analyte-magnetic bead complex binds to the secondary membrane, to produce a visibly perceptible color on the side of the device distal to the skin.
45. The method of embodiment 43, wherein upon affixing the device onto the skin of the subject, bodily fluid is collected through one or more needles, and flows to and passes through the primary membrane, and
    wherein a color change is detected when:
    one or more target hormones and/or analytes complex to the DNA aptamer to liberate the colorimetric dye and produce an optical readout.
46. The method of any one of embodiments 43 to 45, wherein the method further comprises:
    photographing the device;
    sweeping the photograph of the device, or a cropped area of the device;
    creating a vector of color values including the color values obtained from a plurality of horizontal pixel positions on the photograph of the device or cropped area of the photograph of the device;
    identifying the location of the perceptible color depicted within the photograph of the device; and
    calibrating to determine a hormone or analyte level corresponding to a color value.

EXAMPLES

The presently disclosed subject matter will be better understood by reference to the following Examples, which are provided as exemplary of the invention, and not by way of limitation.

Example 1

Identification of a Low-Affinity Binding Protein

HuProt Human Proteome Microarrays (HuProt™ arrays) were used to provide large numbers of unique, full-length, individually purified human proteins on a single microscope slide. Using the HuProt™ arrays, thousands of interactions were profiled in a high-throughput manner. Two HuProt™ arrays were used for identification of a low affinity binding protein. LH-beta was printed on each of the arrays as a positive control. Anti-LH antibodies LH3 and LH6 were selected as the primary antibody samples for probing the microarrays. After blocking, the arrays were probed with the primary antibody samples (10 μg/ml) at room temperature for 1 hour. The arrays were then washed with TBST for 5 min (×3) and probed with Cy3-anti-mouse IgG secondary antibody under conditions optimized for signal detection.

Z Score analysis was performed to identify the target of each primary antibody sample (the non-specific hits bound by the secondary antibody were removed from the analysis of the samples). Sample LH3 recognized the positive control (LH-beta) as the top hit with extremely high specificity. Sample LH6 also recognized the positive control (LH-beta) as the top hit, but with low specificity since it showed equal binding signals on CRK (an adaptor protein for tyrosine kinases).

Figure 5:
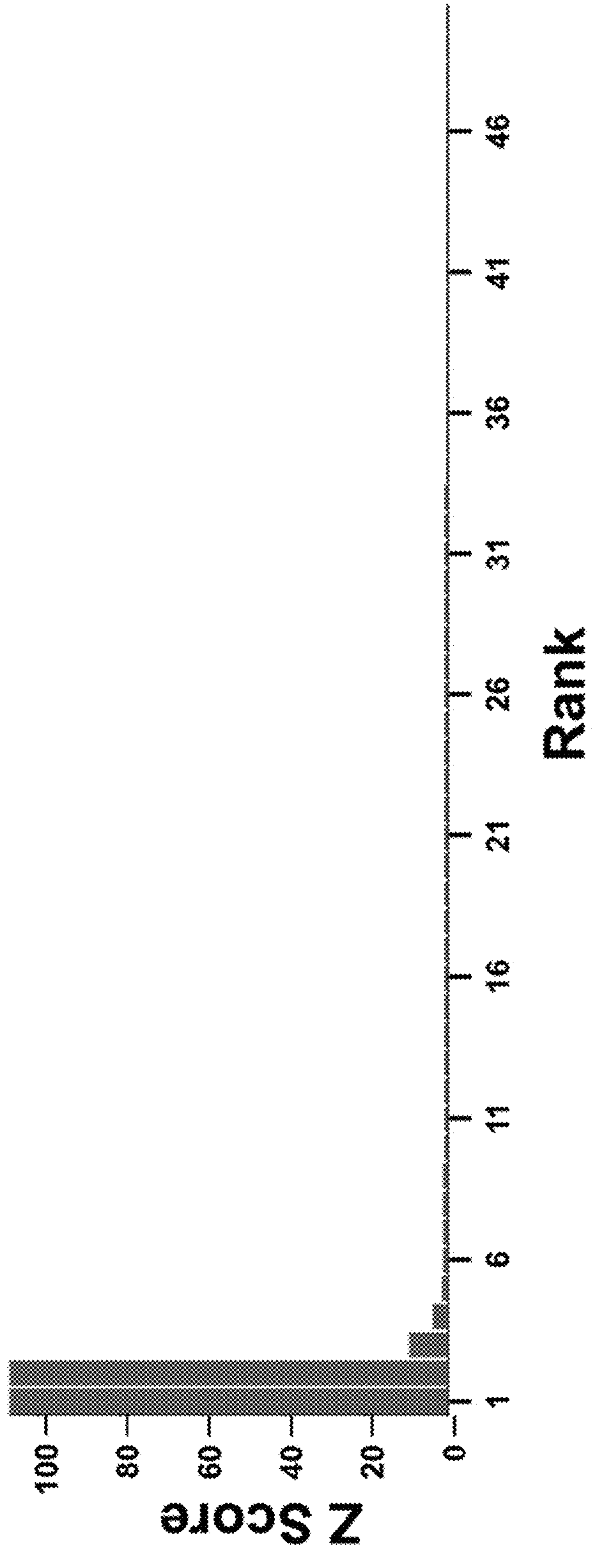
FIG. 5 is a graph showing Hu Prot Protein array results for LH antibody LH6. High z scores for both LH beta and CRK protein, mean the LH antibody can bind to both LH and CRK.

Hu Prot Protein array results for LH antibody LH6 are depicted in Table 1 below. FIG. 5 is a graph showing Hu Prot Protein array results for LH antibody LH6, where ranks 1-5 represent LH6 binding signals with LH-beta, CRK, CRKL, CSRP2, and WIPF1, respectively, and the remaining ranks represent other purified human proteins. High Z scores for both LH beta and CRK protein, indicate that the anti-LH antibody can bind to both LH and CRK.

TABLE 1

| Rank | Protein | F532 | Z Score | S Score |
|---|---|---|---|---|
| 1 | LH-beta | 65535 | 106.993 | 0.000 |
| 2 | CRK | 65535 | 106.993 | 97.762 |
| 3 | CRKL | 5732 | 9.231 | 5.951 |
| 4 | CSPR2 | 2092 | 3.28 | 1.929 |
| 5 | WIPF1 | 911.5 | 1.351 | 0.204 |

Example 2

Magnetic Bead Binding Assay

CRK was demonstrated to be an appropriate low-affinity binding partner for anti-LH antibodies, and it was shown that different degrees of binding can be detected near physiologically relevant concentrations.

Anti-LH Antibodies Specifically Bind CRK

To allow titration of anti-LH antibodies by LH and detection via magnetic beads, a protein that binds the anti-LH antibodies but with lower affinity than LH was needed. This protein serves to immobilize the anti-LH antibodies until they come in contact with LH, to prevent false positive results if antibodies coupled to magnetic beads migrate to the magnetic surface arbitrarily. A binding screen was performed, screening a human proteome library against two anti-LH antibodies. In the screen, both anti-LH antibodies bound LH with high affinity, and one anti-LH antibody also bound CRK (an adaptor protein for tyrosine kinases).

To validate these results and test CRK as a possible low-affinity binding partner for LH, specific binding of CRK by the anti-LH antibody was tested via fluorescence of a secondary anti-mouse IgG. CRK and bovine serum albumin (BSA; a control for nonspecific binding) were immobilized, incubated with anti-LH antibody, and washed. Both samples were incubated with the secondary antibody, washed, and fluorescence detected via a fluorescence-enabled plate reader. Fluorescence was significantly greater with the CRK samples, consistent with the screen and indicating specific binding of the anti-LH antibody to CRK.

Anti-LH Antibodies Preferentially Bind LH

Figure 6A:
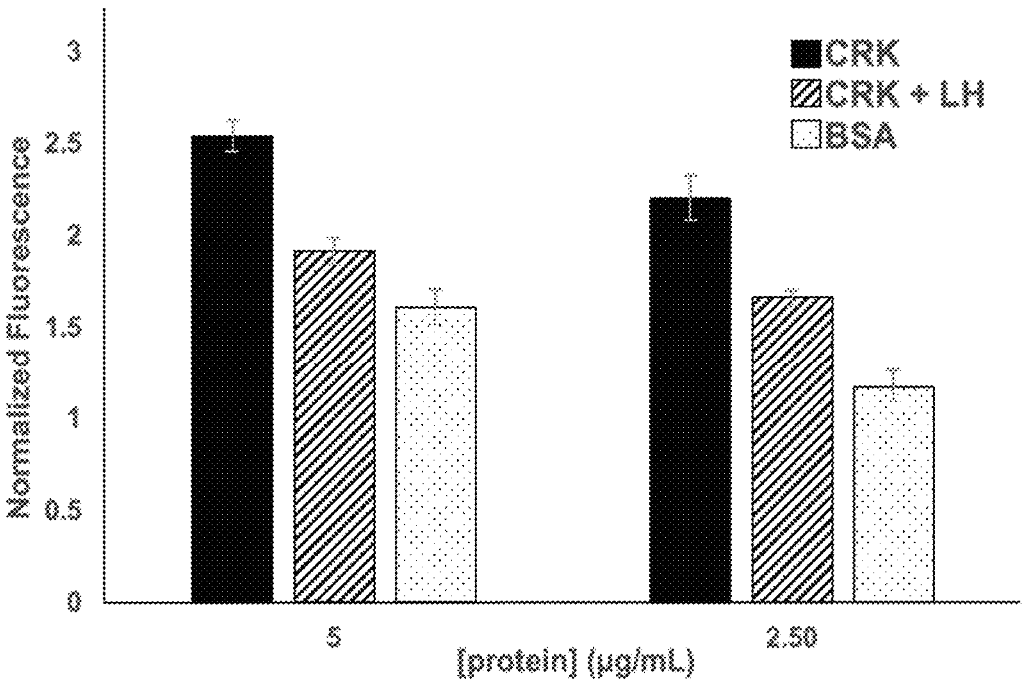
FIGS. 6A and 6B are graphs that show CRK protein is an appropriate low-affinity binding partner for anti-LH antibodies.
Figure 6B:
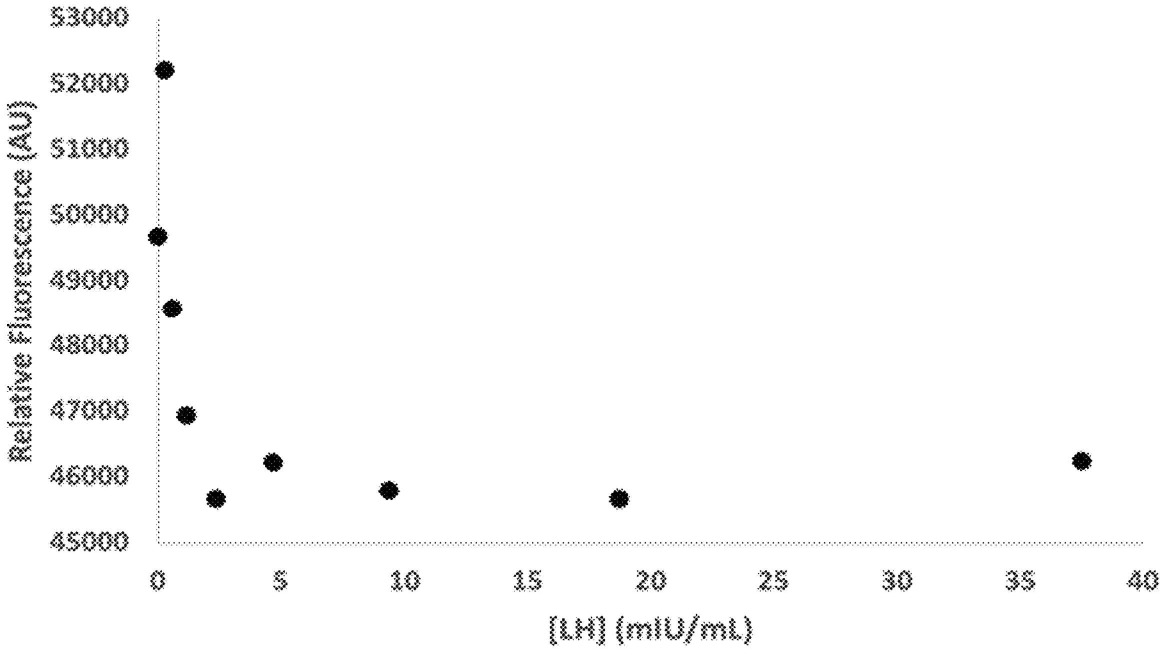

FIGS. 6A and 6B are graphs that show CRK protein is an appropriate low-affinity binding partner for anti-LH antibodies.

To ensure that LH was capable of displacing CRK and preferentially binding the anti-LH antibody, CRK (in two concentrations, 5 μg/mL and 2.50 μg/mL) was immobilized, incubated with anti-LH antibody, and washed to remove excess antibody. At least 4× molar excess LH was added, incubated, and washed to remove both unbound LH and anti-LH antibody bound to LH (as only the CRK was immobilized). Fluorescent antibodies were added to recognize anti-LH antibody remaining bound to CRK and fluorescence was detected.

Comparison to control wells containing no LH revealed that fluorescence decreased in wells treated with LH, meaning that a significant concentration of anti-LH antibody bound LH preferentially over CRK (FIG. 6A). A control containing immobilized BSA instead of CRK served to establish baseline fluorescence, and results were normalized to the fluorescence of the wells containing the lower concentration of BSA. Fluorescence in LH-treated wells did not drop to or below baseline fluorescence, indicating some anti-LH antibody remained bound to CRK. This result was consistent with CRK binding anti-LH antibodies at a lower affinity and demonstrated the binding behavior necessary to titrate anti-LH antibodies from immobilized CRK in a wearable patch.

Displacement of CRK by LH was demonstrated at near-physiological concentrations. 5 μg/mL CRK was displaced by LH at concentrations approximating the physiological range in serum. A binding curve (FIG. 6B) was created using the same fluorescence assay as above with varying concentrations of LH, demonstrating that LH binding to anti-LH antibodies and displacement of CRK is titratable in the range around 25 mIU/mL, the serum concentration required to detect an LH surge with traditional urinary hormone testing [Mikolajczyk et al 2017]. Binding curves may also be fit to equations for protein-ligand binding to determine a dissociation constant (Kd) and necessary concentrations of CRK and anti-LH antibodies.

Magnetic Force and Protein Binding are Competitive

Figure 7A:
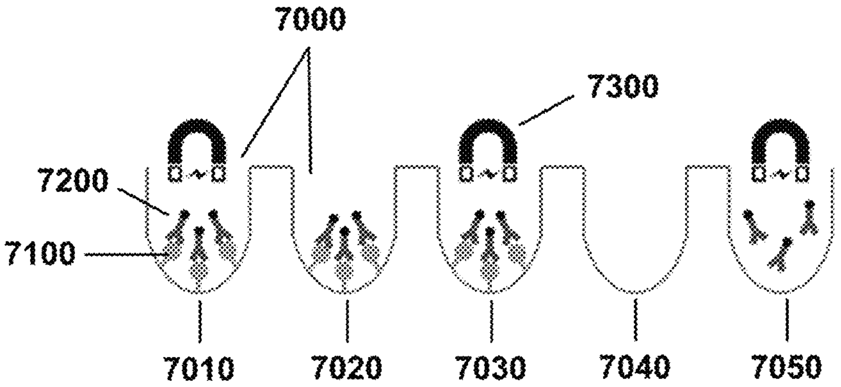
FIGS. 7A-7C show that binding of antibody to CRK can overcome magnetic force as explored in Example 2.
Figure 7B:
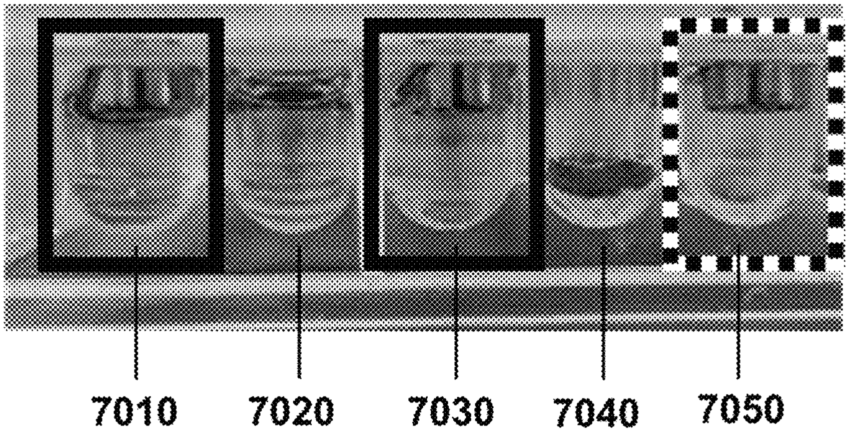
Figure 7C:
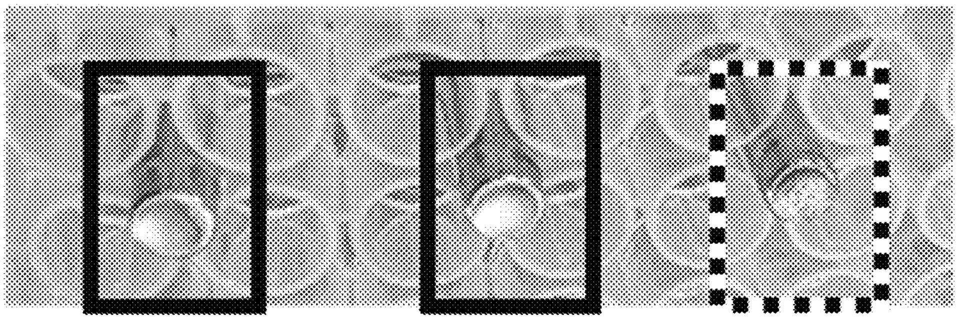

For detection of LH in the wearable device to rely upon magnetic beads only migrating to a magnet upon release by LH binding, magnetic force must be calibrated to be weaker than the force of the protein-protein interactions holding the bead-bound antibodies to immobilized CRK. These protein-protein interactions were found to be stronger than many large commercially available magnets. FIGS. 7A-7C show that binding of antibody to CRK can overcome magnetic force as explored.

FIG. 7A shows the experimental setup for a magnetic bead binding assay demonstrating that binding of magnetic bead coupled antibodies to CRK can overcome magnetic force where, of polystyrene plate with wells 7000, well 7010 represents Sample 1: beads bound to CRK; well 7020 represents visual positive control: no magnet; well 7030 represents Sample 2: beads bound to CRK; well 7040 represents visual negative control: buffer only; and well 7050 represents magnet negative control: no CRK. Wells 7010, 7020 and 7030 were coated with CRK 7100 and incubated with anti-LH antibody coupled to magnetic beads 7200. As a control, anti-LH antibody coupled to magnetic beads 7200 were added to well 7050 with no CRK. Wells were filled with phosphate-buffered saline, and a magnet 7300 designed for use with magnetic beads was inserted into the well approximately 2 mm from the beads at the bottom of the well.

FIG. 7B depicts the results of the magnetic bead binding assay shown in FIG. 7A. Beads in the magnet negative control well quickly migrated to the magnet, while beads/antibody bound to CRK remained at the bottom of the well. In FIG. 7B, sample wells 7010 and 7030 (solid line boxes), corresponding to Sample 1 and Sample 2 of FIG. 7A), remain brown at the bottom as beads do not migrate to magnet, consistent with the visual positive control. The magnet negative control well 7050 (broken line box) demonstrates that in the absence of CRK, beads do migrate to magnet, leaving the well colorless.

FIG. 7C depicts the well magnets of the magnetic bead binding assay. Absence of beads in magnets of sample wells 7010 and 7030 (solid line boxes) and presence of brown beads on negative control well 7050 (broken line box) confirms experimental results. These results confirm that the protein-protein interactions relevant to the wearable design outcompeted significant magnetic force.

We claim:

1. A device configured to be affixed onto skin of a subject and to monitor bodily fluid of the subject for an increase in the presence of target analytes, the device comprising:

one or more needles configured to pierce the skin of the subject when the device is affixed onto the skin;

a primary membrane coated with, on a side thereof distal from the skin, low-affinity binding proteins connected to magnetically coupled primary antibodies, wherein the primary antibodies are directed towards the target analytes, and wherein each magnetically coupled primary antibody comprises a primary antibody coupled with one or more magnetic elements;

a secondary membrane coated with, on a side thereof facing the primary membrane, secondary antibodies, and wherein the secondary membrane exerts magnetic force in a detection zone; and a fluidic channel between the primary membrane and the secondary membrane;

wherein the device is configured such that, when the one or more needles pierce the skin, bodily fluid of the subject flows through the primary membrane into the fluidic channel, wherein, when the bodily fluid comprises target analytes, a target analyte competitively binds to a magnetically coupled primary antibody to form a complex that is released from the low-affinity binding protein on the primary membrane, wherein the released complex (i) traverses the fluidic channel towards the secondary membrane as a result of the magnetic force exerted by or applied on the secondary membrane that attracts the one or more magnetic elements present in the complex, and (ii) binds to a secondary antibody on the secondary membrane, wherein, when a plurality of complexes aggregates in the detection zone, a visibly perceptible color on a side of the device distal to the skin is produced.

2. The device of claim 1, further comprising adhesive.

3. The device of claim 2, wherein the adhesive coats at least a portion of a surface of the device that, in use, is proximal to the skin of the subject.

4. The device of claim 1, wherein the primary membrane comprises a pore size to prevent proteins and/or analytes over 40 kDa from passing through.

5. The device of claim 1, wherein the primary membrane comprises a pore size of about 30 kDa.

6. The device of claim 1, wherein the low-affinity binding proteins are directly connected to the magnetically coated primary antibodies.

7. The device of claim 1, wherein the low-affinity binding proteins are connected to the magnetically coated primary antibodies via conjugation to a carrier protein.

8. The device of claim 7, wherein the carrier protein is bovine serum albumin.

9. The device of claim 1, wherein the low-affinity binding protein is CRK protein.

10. The device of claim 1, wherein the primary antibodies are directed towards the target analytes selected from the group consisting of luteinizing hormone, estrogen, progesterone, and human chorionic gonadotrophin, or a metabolite of any of the foregoing.

11. The device of claim 10, wherein the target analytes are luteinizing hormone, and the primary antibody is an anti-luteinizing hormone antibody.

12. The device of claim 10, wherein the target analytes are pregnanediol glucuronide, and the primary antibody is an anti-pregnanediol glucuronide antibody.

13. The device of claim 10, wherein the target analytes are human chorionic gonadotrophin, and the primary antibody is an anti-human chorionic gonadotrophin antibody.

14. The device of claim 1, wherein one or more of the needles are microneedles.

15. The device of claim 14, wherein the one or more microneedles are configured to remain in the skin upon piercing the skin.

16. The device of claim 15, wherein at least one of the one or more microneedles is configured to be removable from the skin after piercing the skin.

17. The device of claim 1, wherein the fluidic channel contains a buffer.

18. The device of claim 17, wherein the buffer comprises phosphate-buffered saline, saline, or hydrogel, or any combination thereof.

19. The device of claim 1, wherein the fluidic channel has a width between 10 microns and 900 microns.

20. The device of claim 1, wherein the device is a wearable skin patch.

21. The device of claim 20, wherein the device is configured to affix to the subject's torso near the belly button.

22. The device of claim 1, wherein one or more of the magnetic elements are colored magnetic beads.

23. A method of continuously monitoring target analytes in a bodily fluid of a subject, comprising:

affixing the device of claim 1 onto the skin of the subject; and detecting a color change responsive to the presence or increase of target analytes.

24. The method of claim 23, wherein when the device is affixed onto the skin of the subject, the one or more needles pierce the skin and bodily fluid of the subject flows through the primary membrane into the fluidic channel, and wherein a color change is detected when:

the target analytes competitively bind to the magnetically coupled primary antibody to form the complex that is released from the low-affinity binding protein on the primary membrane, the released complex (i) traverses the fluidic channel towards the secondary membrane as a result of the magnetic force exerted by the secondary membrane that attracts the one or more magnetic elements present in the complex, and (ii) binds to the secondary antibody on the secondary membrane, and the plurality of complexes aggregates in the detection zone to produce a visibly perceptible color on the side of the device distal to the skin.

25. The method of claim 23, further comprising:

photographing the device;

sweeping the photograph of the device, or a cropped area of the device;

creating a vector of color values including the color values obtained from a plurality of horizontal pixel positions on the photograph of the device or cropped area of the photograph of the device;

identifying the location of the perceptible color depicted within the photograph of the device; and calibrating to determine an analyte level corresponding to a color value.

* * * * *